(12) United States Patent
Kühnel (10) Patent No.: US 9,364,370 B2
(45) Date of Patent: Jun. 14, 2016

(54) IMPLANT DEVICE FOR THE NON-PNEUMATIC, ADJUSTABLE POSITIONING OF A HUMAN OR ANIMAL BODY PART

(75) Inventor: Thomas Kühnel, Regensburg (DE)

(73) Assignee: Klinikum der Universität Regensburg, Regensburg (DE)

( * ) Notice: Subject to any disclaimer, the term of this patent is extended or adjusted under 35 U.S.C. 154(b) by 313 days.

(21) Appl. No.: 11/661,154

(22) PCT Filed: Jan. 4, 2006

(86) PCT No.: PCT/EP2006/000031
§ 371 (c)(1),
(2), (4) Date: May 22, 2007

(87) PCT Pub. No.: WO2006/072571
PCT Pub. Date: Jul. 13, 2006

(65) Prior Publication Data
US 2007/0288057 A1    Dec. 13, 2007

(30) Foreign Application Priority Data

Jan. 4, 2005 (DE) .................. 10 2005 000 702 U (51) Int. Cl.
*A61F 5/56* (2006.01)
(52) U.S. Cl.
CPC ..................................... *A61F 5/566* (2013.01)
(58) Field of Classification Search
CPC ............... A61F 5/56; A61F 5/566; A61F 2/00
USPC ........ 128/848, 859, 860; 602/902; 623/15.12; 606/191, 196
See application file for complete search history.

(56) References Cited

U.S. PATENT DOCUMENTS

| | | | |
|---|---|---|---|
| 4,978,323 A | 12/1990 | Freedman | |
| 2004/0139975 A1 | 7/2004 | Nelson et al. | |
| 2004/0149290 A1 | 8/2004 | Nelson et al. | |
| 2005/0092332 A1* | 5/2005 | Conrad et al. | 128/898 |
| 2005/0092334 A1 | 5/2005 | Conrad et al. | |
| 2006/0005843 A9* | 1/2006 | Nelson et al. | 128/848 |
| 2006/0207608 A1 | 9/2006 | Hirotsuka et al. | |

FOREIGN PATENT DOCUMENTS

| | | |
|---|---|---|
| DE | 19756956 C1 | 7/1999 |
| DE | 19920114 A1 | 11/2000 |

(Continued)

OTHER PUBLICATIONS

U. Samuel et al., "Prevention of catheter-related infections: the potential of a new nano-silver impregnated catheter", International Journal of Antimicrobial Agents, vol. 23S1, pp. S75-S78 (2004).

*Primary Examiner* — Victoria J Hicks
(74) *Attorney, Agent, or Firm* — Sunstein Kann Murphy & Timbers LLP (57) ABSTRACT

The invention relates to an implantable device for the non-pneumatic adjustable positioning of a human or animal body part, comprising a) at least one elastic element and, optionally, b) an abutment, as well as the use of this device in a method for the treatment of disorders that are caused by the deficient or inadequate positioning of a human or animal body part. In particular, the invention relates to the use of the device for treating sleep-related breathing disorders.

20 Claims, 7 Drawing Sheets

(56) References Cited

FOREIGN PATENT DOCUMENTS

| WO | WO-99/00058 | 1/1999 |
| WO | WO 99/32057 | 7/1999 |
| WO | WO-2004/021869 A2 | 3/2004 |
| WO | WO-2004/032798 A1 | 4/2004 |
| WO | WO-2004/084709 A2 | 10/2004 |

* cited by examiner

IMPLANT DEVICE FOR THE NON-PNEUMATIC, ADJUSTABLE POSITIONING OF A HUMAN OR ANIMAL BODY PART

The invention relates to an implantable device for the non-pneumatic, adjustable positioning of a human or animal body part. In particular, the invention relates to a device for use for the non-pneumatic, adjustable positioning of a tongue body. Preferably, the use of the device is carried out by implantation of the device into the respective tissue. By using the device, particularly sleep-related obstructive respiratory disorders or breathing disorders, respectively, such as sleeping apnea can successfully be treated.

Sleep-related obstructive respiratory disorders are extraordinarily frequent in the Western industrial nations. An estimated 9% of all people are affected by such a disorder. The German Society for Sleep Medicine and Biochronology estimates the number of affected men in Germany to be 200,000. The costs for the treatment of the patients in Germany amount to an estimated € 700,000,000.

In a sleeping organism, musculature experiences a partial loss of its tension. In the area of the airways above the larynx, this leads to a relative instability of the airways, since here, no skeletal parts such as cartilage or bones keep the airways open. In dorsal position of the patient, with decreasing muscular tensional force, the tongue by following gravitational and aerodynamic forces, moves towards the posterior pharyngeal wall and, thus, constricts the respiratory tract on the level of the base of the tongue, the hypopharynx and the velum. In people with healthy sleep, different mechanisms, an adapted nerval regulation of the musculature among others, antagonize a collapse. In about 2 to 4% of the people in the industrial nations, however, repeated (partial) occlusions of the respiratory passage followed by sleep disturbance due to oxygen depletion of the blood and/or arousal reactions (=Arousals) occur during sleep due to a disfunction of this regulation. A cascade of secondary reactions disturbs the sleep and its recreational function. The cardinal symptom of this disorder is excessive daytime tiredness.

At present, sleep-related obstructive breathing disorders are treated by an apparative pneumatic splinting of the airways by means of compressed air which is supplied from the outside by dint of a compressor via a nasal mask (nCPAP). This method has approved itself in routine and is presently considered the gold standard of apnea treatment. Disadvantageous is the uncomfortable sleep by the device that needs to be worn every night, associated with problems that may occur at the mucosas as well as partly a poor acceptance in particular as regards the younger patients. Alternatively, the disorder is treated operatively. However, none of the known methods is free of risks and certain in effect.

A common approach is the reduction of a soft tissue that is considered superfluous or the more or less selectively provoked formation of scars for the stabilization of the soft palate. Various operation methods are available for this. In the radio frequency ablation method, thermal lesions are produced in the tissue of the tongue and in the soft palate by means of alternating current, that lead to scars, which, in turn, leads to a rarefaction of tissue together with stiffening of the surrounding tissue. In the area of the airways between nasopharynx and larynx, the passive support of bone or cartilage, which could prevent a collapse, is missing. The trachea, for example, is stabilized by cartilaginous bridges. They are open on the backside, are elastic to a certain extent, and are connected by a connective tissue-membrane. During uvulopalatopharyngoplasty and the laser-assisted uvulopalatoplasty (UPPP/LAUP), a widening of the faucial isthmus and a stiffening of the soft tissue capable of oscillation is achieved. Another operative principal aims at the correction or alteration of anatomic structures. To this belongs the displacement of muscle attachments, the fixation of the hyoid at the larynx and the forward displacement of the lower jaw or the whole middle face, respectively. In the hyoid fixation, the hyoid is fixed with moderate traction against the larynx. In the forward displacement of the lower jaw, a dentosurgical intervention is carried out during the course of which the lower jaw is sawed apart and is displaced forward by means of metal plates. The corresponding operation procedure is elaborate and not free of risks. In the bimaxillary advancement, upper jaw and lower jaw are sawed apart and the whole middle face is displaced forward. Despite of for the most part good results, the huge surgical effort and the risk of cosmetic disadvantages have prevented a spreading of the method. During tracheotomy, an incision into the trachea meant to bypass the upper airways is carried out. Currently, operative methods are, however, insufficiently effective and/or are too much of a strain for the patient.

In addition, a medicinal device for implantation is on the market which goes by the trade name "Repose" of the Israeli, now US-American company Influ~ENT. Here, a non-resorbable thread is directed through the tongue body underneath the mucosa and is fixed at the inside of the lower jaw by means of a titanium screw. The self-cutting titanium screw is turned in by means of an angular cordless screwdriver after transection of the mucosa. A contact of the tongue with the posterior wall of the pharynx during sleep is prohibited thereby. This system, which is described in the EP 0 998 224, in practice, has yet proven disadvantageous in various aspects. For instance, a non-correctable thread tension exists after operation. The correct length of the thread can only be estimated during operation, wherein, however, no precise indications as to the length of the thread to be selected are available. Moreover, the system is not elastic and, therefore, does not measure up to the form of the tongue which is alterable to a great extent. According to the method set forth by the manufacturer, the thread cannot be positioned straight in a reproducible manner, either. Of particular disadvantage is, that the tension of the thread cannot be dosed dependent on the requirements during operation. A reasonable degree for thread tension could not be determined by own investigations. Furthermore, the loop of the thread compresses the tissue and the blood vessels and nerves running therein. This is additionally aggravated by movements of the tongue, in particular the act of swallowing, wherein the thread is highly stretched. At least during the phase of wound healing, the thread migrates through the glottic tissue in varying, non-calculable degree. Moreover, due to the proximity of the titanium screw to the dental roots there exists the danger of complications. Danger of injuries of the salivary gland excretory ducts exists. Furthermore, the device is not apt to effectively keep other body parts in position, either.

The documents WO 99/32057 A1, US 2004/149290 A1, WO 2004/21869 A2, US 2004/139975 A1, WO 2004/084709 A2, WO 2004/32798 A1, U.S. Pat. No. 4,978,323 A, DE 199 20 114 A1 and WO 99/58 A1 describe devices to keep the airways free. Yet, these devices, among others, have the disadvantage that pre- and postoperatively they can no more be adjusted and that they, for the most part, put at risk significant anatomical structures.

Therefore, the present invention is based on the object to provide a device by which human or animal body parts can be positioned simply, effectively and adjustably and, thus, disorders caused by deficient or inadequate positioning of the respective body parts can effectively and causatively and permanently be treated. The repositioning produced by the device shall be easy to conduct and low in side effects.

The present invention is particularly based on the object of providing a device, by means of which disorders caused by inadequate positioning of the tongue body, in particular sleep-related obstructive breathing disorders, can be treated effectively, with little side effects and in a straight forward way. By means of the device, the tongue shall not be restricted in its mobility or shall only be marginally restricted, and swallowing and speaking shall not be impeded. Furthermore, the device shall permit an adjustment that is easily performed in order to cope with changing requirements concerning the disease or disorder. In addition, the implantation of the device shall be technically simple. Preferably, the device shall be implantable by customary routine instruments of an ENT-surgeon.

This object is solved by an implantable device for the non-pneumatic adjustable positioning of a human or animal body part, comprising a) at least one elastic element and optionally, b) an abutment or counterbearing, as well as the use of the device in a method for the treatment of disorders that are caused by a deficient or inadequate positioning of a human or animal body part, in particular for the treatment of breathing disorders, sleep-related respiratory disorders, obstructive snoring, glossoptosis and similar diseases.

Surprisingly, it was found that a system which has at least one elastic element advantageously is suitable for the non-pneumatic adjustable positioning of a human or animal body part. The system optionally also contains an abutment.

As far as the system only consists of an elastic element, this may be configured in a form of a clip ("Spange") or a ring. The elastic element may further be of one or several parts and in this case is provided together with an abutment.

The elastic features of the device of the invention should come close to the ones of the surrounding tissue. In order to reduce the probability of an extrusion and by still yielding the desired counterforce to the critical collapse pressure and the gravitational force, the device of the invention must contain an elastic element which is reversibly anchored in the body part that is to be positioned. The elastic element allows the adjustment of the necessary force in the desired direction. By stretching of varying intensity, the force can be modified. That way, also a tension that was not optimally set during the first intervention can be corrected at a later point in time. The connection of the elastic element with further elements of the device of the invention may be effected by locking or adhering.

The elastic element allows a discrete adaptation of the implantable device to the respective circumstances of the organism in which the implant is to be inserted.

The initial tension of the elastic element can be varied by a small intervention in local anesthesia, wherein the elastic module of the device may be replaced where appropriate. In doing so, the initial tension of the elastic element as such (for a one-piece device) or the positioning of the elastic element as regards the abutment are altered. The device may be implanted via an access from the outside, i.e. via a skin incision. The elastic element allows a continuous or gradual adaptation of the system to different anatomic circumstances of the patient as well as to the requirements of the patient which change throughout life. By the device, a force is exerted against the gravitational force and against the critical collapse pressure, which force is bigger than the weight of the tongue but smaller than the muscle force developed by the tongue itself during speaking or swallowing, and corresponding forces during the positioning of other body parts, respectively. Furthermore, the device of the invention for the treatment of respiratory disorders may be implanted from outside, i.e. submentally, whereas the corresponding device of the prior art (Repose) is implanted enorally, i.e. across the teeth towards the floor of the mouth.

The arrangement of the components in the elastic element may be such that in sagittal direction movable parts of the floor of the mouth and of the tongue accommodate the elastic components, and the anatomic structures that are less movable in sagittal direction accommodate the rigid or less elastic parts of the element. Preferably, the more elastic part of the band is adjacent to the anchor, a more rigid part of the band to the abutment. The connection of the components may be affected by adhesive sealing or by inserting a material of lower elasticity into the elastic element (amoring, "Armierung").

In case that the device according to the invention only consists of an elastic element, the latter is preferably in a ring-shaped form and, particularly preferably, is designated for implantation in the pharynx. It proves particularly advantageous for the treatment of sleep-related breathing disorders. The respiratory duct unlike at other sides (trachea, larynx, nose) is not supported by cartilage or bones in the collapse segment. In people that are awake or have healthy sleep, the muscle tension guarantees for the opening of the collapse segment. A sick person does not have a sufficient muscle tension, so that the atmospheric pressure compresses the respiratory duct. Different forms of collapse are observed. Here, primarily the tongue drops backwards. A circular implant bears the advantage that it resists the critical collapse pressure and yet enables the intended collapse of the awake person by means of its elasticity. Such a circular implant may consist of several small circular implants or may consist of a round body. The latter consists of a biocompatible material, preferably plastic, i.e. silicone.

The implantation of a ring-shaped device is practicably carried out by placing a path finder (probe) (strong thread) and a subsequent pulling through of the implant underneath the mucosa or the superficial muscle layer. The physiological main movement (swallowing, speaking) is an approximation of the tongue base to the posterior wall of the pharynx. Hence, the implant must have a predetermined breaking (kinking) point at the sides. This is achieved by a site with particularly weak material application. The dimensioning of the clip, which may be closed in a preferred embodiment and then has the shape of a ring, basically depends on three factors. Here, it is referred to the implantation in the pharyngeal tissue. The factors are the desired reset force, the individual configuration of the throat and the amount of tissue that shall be prevented from collapse by the clip. Here, the clip is put into relation to the spinal column. In the area of the spinal column, the clip is open or has its lowest strength of material, respectively. Laterally, the clip ideally has predetermined kinking sides in order to admit the backwards moving of a tongue upon swallowing and speaking. The elastic reset force equals the pharyngeal closing pressure during an apnea or it is slightly above. In direction to the base of the tongue, the clip is wider in order to sufficiently engage tissue. In the following, an example for a possible dimensioning of a clip made of permanently implantable silicone Nusil Shore hardness 75 is given:

| | |
|---|---|
| Maximal width: | 15 mm |
| Minimal width: | 1 mm |
| Length: | 75 mm |

| | |
|---|---|
| Maximal material thickness: | 2 mm |
| Minimal material thickness: | 0.5 mm |
| Opening of the clip: | 20 mm. |

By thinning out the silicone towards the ends of the clip, the reset force of the implant at this site is reduced thus, until it approximately corresponds to the elastic features of the tissue and with it the probability of extrusion is reduced. The elastic element is apt for sole implantation, if its elastic reset force is sufficiently large to resist a pathological collapse pressure which predominantly acts backwards and from the side towards the middle. In the treatment of sleep-related breathing disorders, a ring-shaped implant has the advantage that the forces taken up, which reach their maximal values during the act of swallowing, are not directly deflected into the tissue, but are taken up from the backside portion of the implant.

The device of the invention may also be configured multi-part. A multi-part implant is characterized by at least one shapeable movable component and one non-movable component. The non-movable component serves as an abutment and forms the connection to a referential point, for example a bone structure such as the lower jaw. The shapeable movable portion of the implant is referred to as an elastic element. This elastic element itself may be of one piece or may be multi-part. In a preferred embodiment, the elastic element is in form of an anchor and a band, respectively. In the following, this embodiment shall now be described in more detail.

The elastic element can have any shape and, preferably, exists in form of a band or strap, respectively. All materials which satisfy the criterion of permanent elasticity, for example silicone, composite materials, steel springs, are suitable for this. A thread-shaped elastic element, which is also called anchor thread, may be designed as a band or round body. For radiological methods, the thread-shaped element may be made radiodense by incorporations of different contrast giving agents such as barium sulfate, as long as the material features and the biocompatibility are not influenced negatively. Preferably, the elastic element is furnished with a cover. This cover forms the barrier against the body part and may e.g. be of polyurethane, a silicone foil or polyethylene. That way, the elastic element can move within the necessary boundaries without being restrained by scars. The cover shall be non-resorbable, shall promote integration into the tissue and shall be bacteriostatic/bactericidal. In case the elastic element is in a silicone embodiment or in a corresponding material embodiment, a cover is not necessary.

In case of a silicone embodiment, integration to the tissue can be prohibited and the movability relatively to the environment can be maintained by a particularly smooth surface. This can e.g. be obtained by the electric discharge machining method during the production of the nest. The silicone may be doped with silver ions (nanosilver, Samuel U, Guggenbichler J P: Prevention of catheter-related infections: the potential of a new nano-silver impregnated catheter. Int. J. Antimicrob Agents, 2004 March; 23 Suppl. 1:p. 75-8.) in order to yield a bactericidal/bacteriostatic effect.

The band-shaped elastic element can be of different design. For example it may be designed as a polyhedron (for example as a cuboid), as a rotational body or as a part of a rotational body. Furthermore, it may be rounded at the edges. Moreover, the band at one or several sides may have recesses or raised parts. These may, for example, be cavities, holes, grooves or neps. In a further embodiment, the band has one-sided or two-sided round, oval or polygonal cavities of a conic or a cylindrical section for taking up a locking bolt/screw reaching through the whole section, or for taking up a bolt that only partly reaches through the band. In a further embodiment, the band has round, oval or polygonal holes (through holes or passage apertures, respectively) of conic or cylindrical cross-section which reach through the section of the band. In those, a bolt or a screw can be inserted without problems.

In a further embodiment, the band has round, oval or polygonal openings reaching through the section of the band that have a conic or cylindrical cross-section. By means of a thin material lamella in the middle of the cross-section, the tissue is prevented from fully-growing through the hole. This lamella can simply be removed with a conic instrument (punch). The lamella of varying thickness can seal the opening unilaterally. The locking bolt may reach through the band completely or only partially.

In further embodiments, the cavities/openings are arranged in a close distance, which results in an approximately continuous adjustment mechanism. The cavities or openings may also be arranged in a bigger distance, e.g. of 18 mm, so that a tearing out of the band is getting unlikely. The cavities or holes may have as small a diameter that they do not have any noticeable influence on the stability of the band. By stretching, the passage of the screw/a bolt is enabled.

A further embodiment of the band-shaped elastic element represents an elastic band having a fish scale structure ("Fischschuppenstruktur"). This embodiment may be made of a permanently elastic material or yet of a resorbable material. In this latter case, in the long-run, there follows a scar which imparts the desired features to the surrounding tissue. Such bands are commercially available e.g. from the company of Johnson & Johnson. This special surface structure allows a movement after implantation in the tissue only in one direction. In one embodiment, such a band, for example at the base of the tongue, is thus wide that further elements of the device can be omitted and that this band can be used as the sole implant. In the embodiment which is intended for implantation in the area of the mouth, the alignment of the fish scale surface is counter-equal to the alignment at the base of the tongue. The fish scale band is preferably pulled under the hard periosteum. At this site, an unwanted movement towards dorsal is practically impossible, so that in the effect, a compression of the tissue can be achieved thereby.

According to a further embodiment, the elastic element/elements have barbed hooks at their tip, which stays in the tissue. These barbed hooks prohibit the dislocation of the implant under traction.

According to a further embodiment, the elastic element has a spring constant, which is obtained by a specific material thickness. Here, the elastic element is made of a homogenous material of variable material thickness. Preferably, the elastic element consists of silicone and the force acting on the tissue of the tongue is 3 N upon elongation for 10 mm. The width of the elastic band is about 4 mm. An implant having a smaller diameter of the elastic band may be produced in case that a smaller force is required in a certain patient constellation.

According to a further embodiment, the spring constant of the elastic element is achieved by a specific type of material. Smaller reset forces are achieved by silicone of a smaller Shore hardness, bigger ones by silicone of higher Shore hardness. The elastic element may also consist of different materials, for example silicone of different hardness or joint materials such as metals, plastic, fabrics or composite material.

According to a further embodiment, the desired spring constant of the elastic element is achieved by the co-action of various components. For example, a steel spring or a thread may be introduced into the elastic element in its whole length or in partial sections. That way, a combination of elastic and less elastic components is generated. Less elastic can also mean rigid. The fine adjustment is achieved by a respective pre-elongation. It is object and feature of the elastic element to achieve an elastic force having a defined or definable spring constant upon turning by the movement of the tongue relatively to the posterior wall of the pharynx, to lower jaw and upper jaw and other structures of the pharynx.

In an embodiment, the elastic element is in form of one or more tubes. For implantation, a trocar is necessary, which encloses a channel through which a wire can be pushed forward into the target region of the tongue. The channel comprises a bend at its end, which releases the wire in the desired angle. In one embodiment, this angle is 90°. The trocar consists of a cover, a tip, an outlet opening at the side and an inlet opening. At the side of the outlet opening, the trocar has the biggest diameter (for example 10 mm), in order to supply space to the bend of the leading channel. The wire is pushed forward via the trocar in a sagittal direction of the tongue from submentally up into the submucosal space. By the form of the interior of the trocar, it is then deflected towards the side upon leaving the trocar. The wire intrudes through the musculature all the way to the lateral edge of the tongue. The compounds introduced via this route into the tongue can retroactively be influenced in their elasticity. The pretension of the tube is altered by introducing a core. This core can consist of any material. In a preferred embodiment, it consists of metal. Further suitable materials are textiles or plastics (for example polyurethane, polytetrafluoroethylene or thermoplasts).

In another embodiment, the rigidity is increased by putting the elastic element under tension. The core described can be fixed by a thread ("Gewinde") at the tongue-side edge of the elastic tube by gluing or another mechanic mechanism which is common in the art. At the chin-side edge, the tension of the construction is set. This is for example possible by means of a thread ("Gewinde") on the core, over which a nut is screwed that has a greater outer diameter than the elastic tube. By tightening the nut, the core is shortened relatively to the elastic tube. A tension arises between tube and core, which results in an increased rigidity. The rigidity of the core can also be increased by thermal or chemical methods.

A further element of the system is an anchoring device or an anchor, respectively. This anchoring device can have any shapes, wherein the basic principal is that the force is on the one hand transferred to as big an area of tissue as possible, and that on the other hand the anchor itself shall have a small surface. In doing so, the possibility of a colonization or infection of the foreign material with pathogenic germs as well as the foreign-body reaction shall be kept as small as possible. A feature important for the function is the distribution of force towards the periphery of the anchor. There exists a differently established tendency e.g. of the sidewalls of the pharynx to collapse towards the middle. By its form, the anchor shall counteract that. The anchor, which preferably is designed in a disc-shape, preferably has a material thickness or strength of material, respectively that decreases towards the peripheral region. At marks it may be shortened corresponding to the individual anatomic situation. The ends preferably terminate slimly so that they may be introduced more easily into the tissue. At the end of the wings of the anchor, there are portions that may be cut off by the operator (operating surgeon) in order to account for individual anatomic circumstances, distinguished by a lower material thickness.

In preferred embodiments, the anchoring device constitutes a round, elliptically formed oval disc or plate, respectively. Perforations differing in number and size may be present in order to improve the integration of the device into the tissue. Furthermore, the anchoring plate may be doped with an image-producing material such as barium sulfate in order to allow for an image-morphological or radiological examination, e.g. whether the implant lies intact and in correct position in the body. The anchoring plate may be doped with silver (nanosilver) or with another material, which counteracts the colonization of the implant and/or an infection of the surrounding tissue. A further embodiment is an anchor, which unfolds according to the principal of an umbrella. Thereby, the implant may be grafted without an open connection from the outer wound for example at the chin and base of the tongue. The time for surgery could be reduced that way, which minimizes the danger of infections as well as the pain to be expected. Here, the wings of the anchor are connected to an elastic strap and push into the tissue when they are released.

Figure 1:
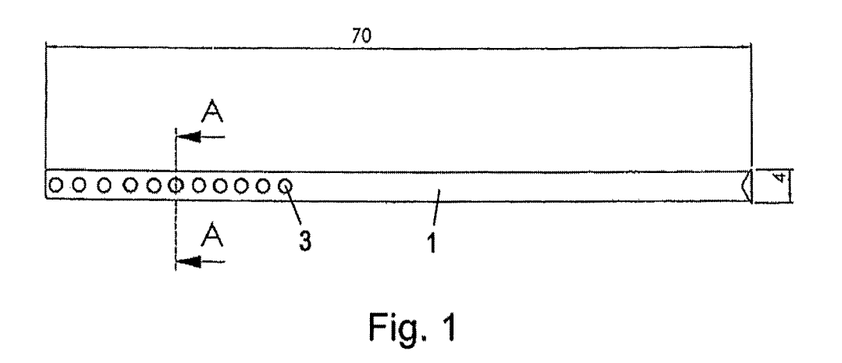
FIG. 1: Elastic element 1 in the form of a band. The specifications are in [mm]. On the right hand side the thickening is drawn with a width of 4 mm and a height of 2 mm, which prevent the escape from the anchoring plate. Section AA shows a hole 3 in the band that takes up the arresting pin or screw, respectively, of the abutment.
Figure 2:
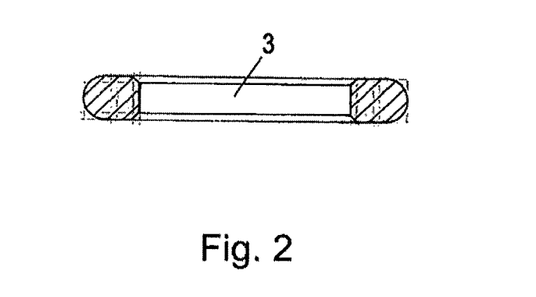
FIG. 2: Section AA of FIG. 1.
Figure 3:
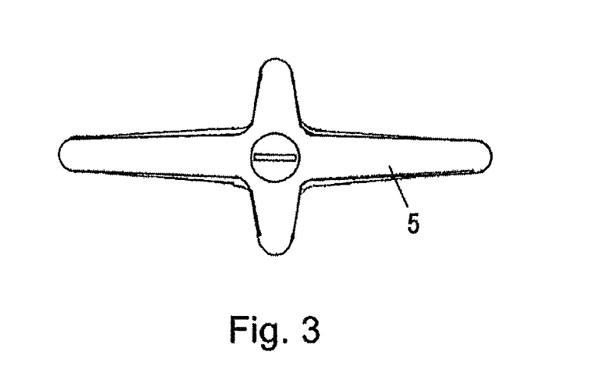
FIG. 3: Anchoring plate 5 in top view.
Figure 4:
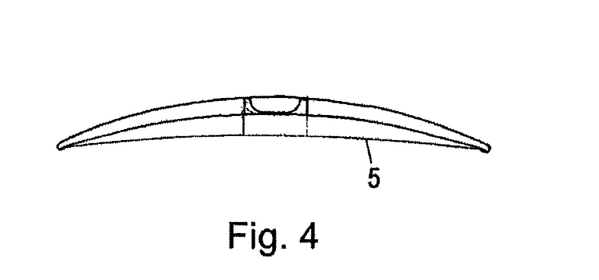
FIG. 4: Anchoring plate 5 in cross section.
Figure 5:
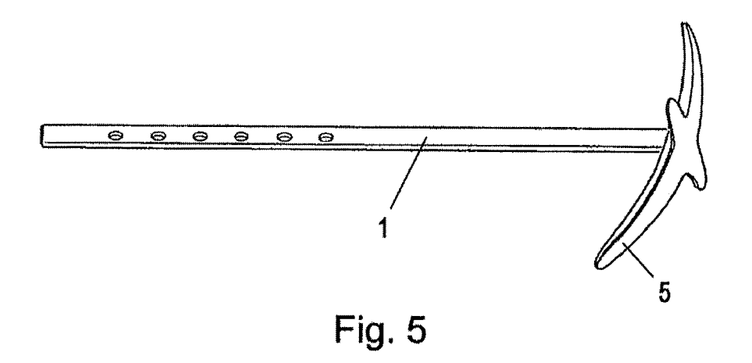
FIG. 5: Anchor 5, connected with elastic band 1.
Figure 6:
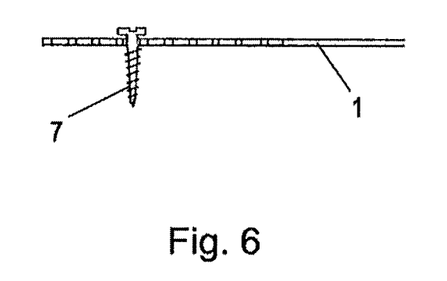
FIG. 6: Elastic band 1 with screw 7 connection to the bone as abutment.
Figure 7:
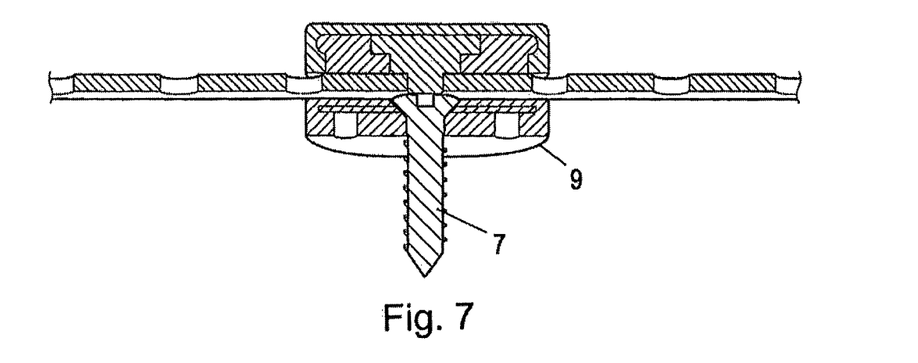
FIG. 7: Abutment 9 in 3D-cross section.
Figure 8:
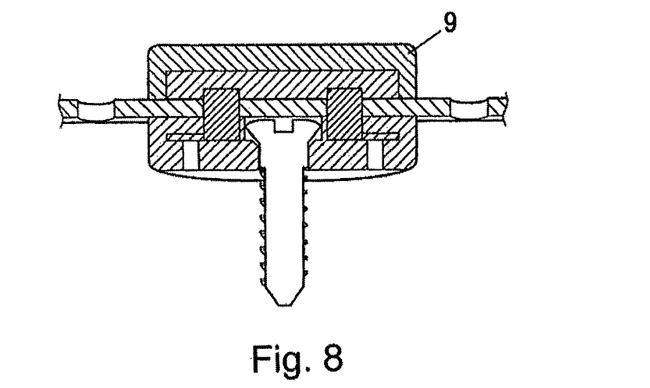
FIG. 8: Cross section of the abutment 9 according to FIG. 11 in the 3D-top view.
Figure 9:
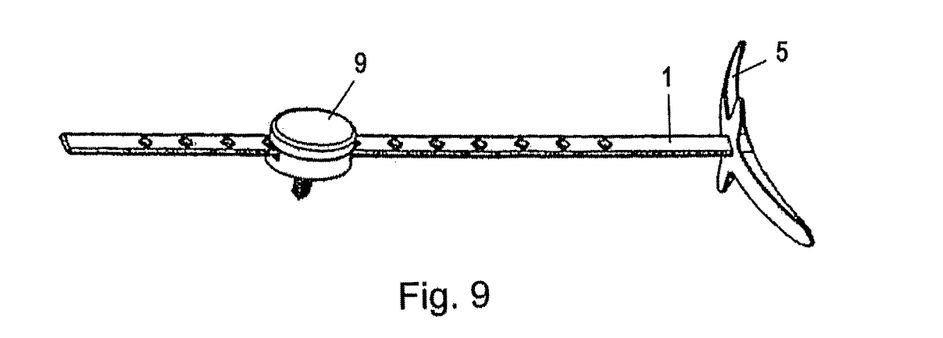
FIG. 9: Implantable device with completely closed abutment 9 and elastic band 1 in the oblique top view.
Figure 10:
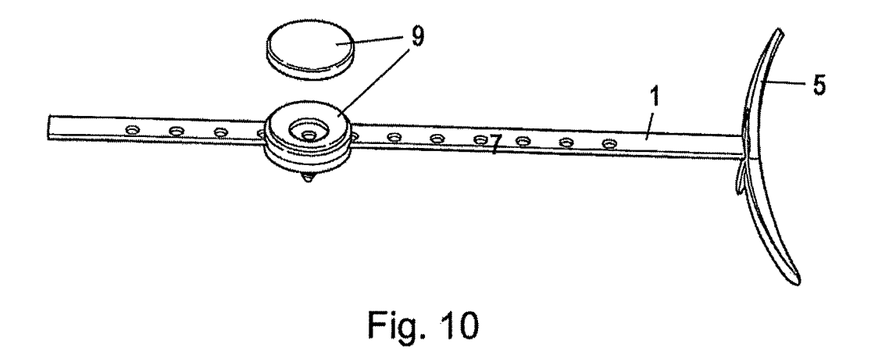
FIG. 10: Corresponds to FIG. 9 with completely opened abutment 9 in the 3D-oblique top view.
Figure 11:
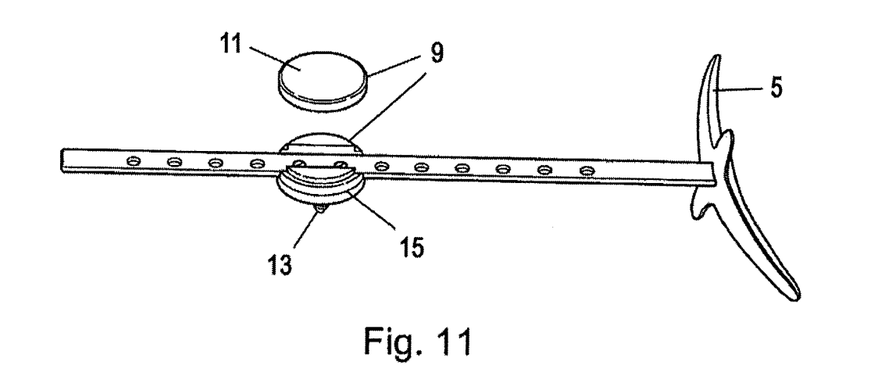
FIG. 11: Embodiment of the abutment 9 in which the band 1 can be lifted out of the opened abutment. The locking cap 11 serves for the fixation of the band 1 in the leading channel in two planes. The locking bolt 13 is not integrated into the cap, but into the base body 15. The illustration shows the completely opened abutment in the 3D-oblique top view.
Figure 12:
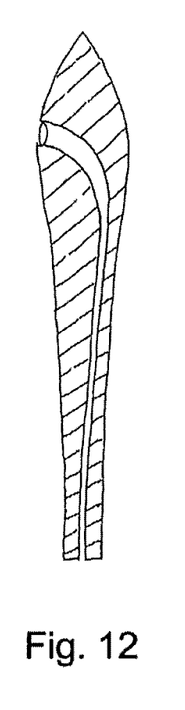
FIG. 12: Trocar with guide channel; exit for the guide channel at the thickened end, input opening at the end opposite to the tip.
Figure 13:
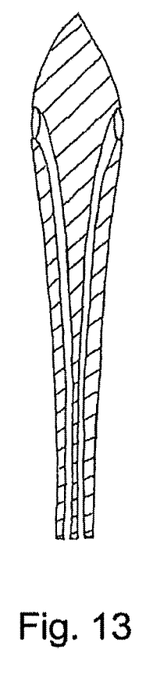
FIG. 13: Trocar with two guide channels.

Preferred embodiments of the anchoring device are depicted in FIGS. 3 and 4. The ends of the anchoring device may terminate pointed or blunt. Ends with sharp edges are to be avoided, since they favor an extrusion. Pointed ends simplify implanting the device into the tissue. The farther the anchoring device according to the invention is dimensioned laterally, the more soft and blunt the edges need to be. Upon implantation into the movable part of the tongue (landmark linea terminalis), the anchoring device must have a smaller or the same width as the tongue. Upon implantation in the unmovable part of the tongue (landmark glossotonsillar groove), the anchoring device of the invention may be wider and may support itself at the sidewall of the pharynx or the posterior wall of the pharynx. Moreover, the anchoring device may be straight or bent, bend forward concavely or convexly. The craniocaudal (perpendicular) legs or ends, respectively, may be bent in the opposite direction. The perpendicular legs may be of varying length, they may yet be shortened, optionally be developed only stub-shaped. In case that the anchoring device is shaped convexly towards the front, it describes the desired form of the respiratory duct and supports the same. The forces that act from the side towards the middle are taken up solely by the rigidity of the material. Also without forward traction, the airways are kept open within these boundaries. The farther the device reaches towards the side or upwards and downwards, respectively, the more tissue is prevented from the collapse. The bend of the device can be based on the natural bend of the tongue, so that no pretension of the device is required. The device may be bent more strongly and may also be made planar. An anchoring device having a concave form is not brought into the desired form until the elastic band pulls forward, so that in this case the elastic band is an indispensable component of the device according to the invention. The pretension of the device causes greater forces at the ends of the anchoring device.

According to a further embodiment, the anchoring device is characterized by anchor flukes which are made such that their forward-turned concave-bow-form spread up the sidewalls of the pharynx, if the traction in direction to the point of the chin increases. A force perpendicular to the direction of the traction is generated thereby. According to a further embodiment, the anchor flukes are made such that the elasticity modulus at the ends corresponds to that of the surrounding tissue and, therefore, an extrusion is prevented. This can for example be achieved in that the anchor flukes terminate thin towards their free ends.

According to a further embodiment, the anchor together with the elastic bend may be produced in one piece.

Generally, the anchoring device may be of any material, provided that the material is biologically-compatible and suitable for the permanent disposition within the body.

Examples for materials are silicones, polyurethane, polytetrafluoroethylene. An exemplary trade product is the material Nusil 4870 LSR implant silicone. Since silicones are offered in varying degrees of hardness (Shore 45 to 70), the implant can be manufactured completely of one type of silicone or in parts of different silicone. The band may be made completely of an elastic material, partially or completely of a non-elastic material.

Generally, the anchor may obtain stability by material features, material thicknesses or strength of material, respectively, and material form. One embodiment consists in bending the anchor flukes in a direction opposite to the pulling direction. The approximation to a spherical segment promises the greatest rigidity with the lowest material usage. Furthermore, the desired material rigidity of the anchor and/or the elastic element may be obtained by common methods of statics such as reinforcing ribs.

The size of the anchoring device is basically determined by the anatomic circumstances at the respective site. An anchoring device for use for positioning a human tongue body, for example, has the following dimensions that correspond to the common variability of the human or animal tongue body.

In case that the elastic element is provided in form of a band, it may be adhered with the anchoring device. The anchoring device may also be manufactured as one piece together with the band-shaped elastic element. The band-shaped elastic element may have a thickening at the base of the tongue. In this embodiment, it may be pulled through an aperture of the anchoring device and finds footing in a recess at the anchoring device. The recess is constructed such that the band-shaped elastic element can slide through, whereas the thickening at the end cannot. That way, the elastic element may be exchanged in case of a defect or if another material feature is desired. Band-shaped elastic elements may have different Shore hardnesses and different dimensioning. That way, depending on a patient-specific demands, the right size of the elastic element can be employed.

The elastic element in shape of a band may be dimensioned differently. For a tractive force of 1 N that is to be expected for the implantation into a tongue body, the elastic element shaped in form of a thread is 3.5 mm wide and 0.75 mm thick. During the operation, the operating surgeon has the possibility to shorten the anchor flukes and thus adapt them to the anatomy of the base of the tongue.

The further element of the system, the abutment, may exist in any technical realization. Preferably, it is in form of a screw. This should have a depth stop, so that the operator automatically and compulsorily finds the correct screwing depth. There should be no thread ("Gewinde") in the free portion in order not to harm the abutment to be implanted at the sharp thread. The screw must be of a tissue-compatible and inert material in order to be as save as possible against rejection. The preferred material is pure titanium. Furthermore, the screw should be self-cutting in order to minimize the operative effort (thread cutting). It must be strong enough so that it is not inadvertently twisted off (≥2 mm diameter) or not to suffer fatigue fracture. The screw head should be round, oval or rectangular. The elastic element can on the one hand easily be hooked in with preferably also rectangular, round or conical recesses upon longitudinal positioning of the screw, and on the other hand cannot inadvertently slide off in case of a transverse, i.e. arrested, screw head. The screw head is prepared for accepting a common screwdriver used in osteosynthesis surgery. The screw may also be designed in hook-shape. The type of screw used as an abutment is not critical and may easily be selected from a person skilled in the art in correspondence with the present disclosure on the basis of his knowledge in the art. The screw should resist the forces that are transmitted to it in a permanently stable way. Moreover, it must be of a sufficiently large dimension, so that the elastic element that is hooked in cannot loosen. Furthermore, it must yet be sufficiently small so that the patient does not perceive it as disturbing. Examples for this are a screw diameter of ≥1 mm and ≤5 mm, a length of ≥3 mm and ≤30 mm. The thread may be self-cutting or non-self-cutting. The hole taking up the screw is pre-drilled, the thread is cut, the screw is turned in. The screw may have a circular head, which has the advantage that it can be produced inexpensively and uncritically, and that a malposition by incorrect turning-in is unlikely. Moreover, the screw may yet have a head which is configured flat in the side view (lentil head). The head may also be larger, which has the advantage, that thereby, the elastic element is reliably prevented from sliding off. A screw having a head which is configured flat in the side view (lentil head) can additionally fix a washer on the device of the invention. The washer may assume all forms and consist of any biocompatible materials. Preferably, it consists of a foil. The foil must be stiff enough in order to prevent a sliding off of the elastic element according to the invention and must be soft enough in order to prevent irritations of the patient. Preferably, the foil takes a circular shape and has a diameter that slightly exceeds the width of a, for example, band-shaped elastic element. A preferred example for a dimensioning of the foil is a diameter of 4 mm and a thickness of 0.5 mm.

The screw may have a head which, in top view, is symmetrical, oval, rectangular or elliptic. It may have a hook-shaped head. The shaft may be shaped conically or cylindrically.

Preferably, the screw at the head and is coated with silicone at the part which emerges from the bone (example tooth implant).

The abutment may also consist of a stemmed silicone head, over which the band is hooked in with its slot-shaped opening.

Instead of a screw, the abutment may also have the form of a simple clamping. For this, the elastic element would need to have a structured, for example saw tooth-like surface, in order to pull it in one direction through a corresponding opened clamping and to prevent a sliding back.

By means of the screw, the actual abutment is retained at the bone. In doing so, the abutment consists of a silicone block that, for taking up the elastic element, contains a drill hole which exactly corresponds to the diameter of the band. By means of a cap which covers the block and which contains a central pin, the silicone band is attached in the individually determined position. In case a correction or repair is required, it is sufficient to uncover the block and draw off the cap and newly adjust the band. After putting on the cap again, the closing of the wound is effected. At the edges, the cap may form the closing to the screwed-on block with a circumferential lip. The cap may be of a smaller area than the block. The cap may be inserted into the block such that the surface is flush. The pin, which is attached to the cap and which makes the connection between block and band, with its free end can be taken up in a recess of the block.

The elastic element may be used in different material thicknesses and material hardnesses. Also combinations of materials of different hardness (e.g. different silicone hardnesses) may be used. The width of the area and the material thickness or strength of material, respectively, can be configured according to the needs in order to, for example, individually adapt the implant to patients having different neck sizes.

A further possible form of the abutment is an encapsulated coil or an eccentric over which the elastic element is put. Then, it could be readjusted by means of a screw head via a stab incision. The abutment may also be provided in form of an electromechanical locking, which produces force closure at night but is disengaged during the day in order to turn off any influence on the body part to be positioned.

In a further embodiment, the abutment can be screwed on the bone or can be integrated into a cavity of the bone. The abutment may also be partially integrated into the bone, i.e. a part is not integrated into the bone and is connected to the elastic band, the other part grows into the bone. Furthermore, the abutment may be attached with a screw at the bone in one part. In a further embodiment, a base may be attached at the bone with one or several screws and the abutment is hooked into the base and arrested. A corresponding closure cap or locking cap, respectively, may serve for attaching the band in one plane or for attaching the band in two planes. Moreover, the elastic band may be arrested in the abutment by means of one or several bolts. These bolts may be attached in the base body or in the closure cap. In doing so, the closure cap may be completely separated from the base body or be connected with it via a material bridge. In this case, it is tilted onto the base body, over this bridge, which serves as a hinge.

In a further embodiment, the locking cap has a lip directed inwards, which prevents the intrusion of liquid into the abutment and serves for the safe attachment of the cap at the base body. For the adjustment/correction of the band tension, tools taken from osteosynthesis instruments are not needed.

In a further embodiment, the closure cap has a lip directed outwards which prevents the intrusion of liquid into the abutment and serves for the safe attachment of the cap on the base body. The locking cap may be fixed with silicone adhesive or may be screwed on.

In a further embodiment, the elastic band is guided through a liquid-tight channel of the abutment. At the free end, a closure piece is clamped on or glued on. This closure piece may fittingly be threaded over the band and attached at the predetermined position, or it is guided over the band and is attached. In this embodiment, the band does not have notches, grooves or holes.

The abutment may consist of different tissue-compatible materials. Preferably, bioinert materials are used. Particularly, preferred are silicone of different degrees of hardness, optionally doped with x-ray contrast agents and/or nanosilver, polyethylene, polyamide, polyester, titanium, other metals, ceramics, composite materials, for example also coated with gold.

In a further embodiment, the abutment can also be realized with a self-sealing titanium screw and filiform holes of the elastic band. Here, the screw locking the elastic band catches a thread which is placed in the screw head of the screw that fixes the abutment block at the bone.

The size of the abutment corresponds to the body part to be positioned, for example the size of the abutment for a device for positioning a tongue body, e.g. a screw, is 8 mm in length and 2 mm in diameter. A screw head, for example, has a smallest diameter of 4 mm and a largest diameter of 7 mm.

Upon implantation into a tongue body, the device according to the invention has the advantage that the anchor stretches open the lateral pharynx and also exerts a forward traction towards cranial and caudal. With that, the collapse is prevented in three dimensions. By stretching the elastic element, i.e. the anchor band, the operator can change the force opposing the force of gravity. With an also provided force measuring device (tensiometer or spring scale) a basic setting can be performed. By inspection, e.g. with optical aids (flexible fiber optics, fixed angle optics), the movement of the tongue body away from the posterior wall of the pharynx can be observed. As soon as the patient is relaxed in anesthesia, the maximum variant of the sleep-related muscle atonia, which is the pathogenic principle of sleeping apnea, can be simulated. That way, the tension of the elastic module can be set thus that the tongue lifts off from the posterior wall of the pharynx. During corrections, that may be necessary as the case may be, there is the possibility to hook in the elastic element at the screw at another position at the abutment and with that increase or decrease the force.

The device according to the invention may also be produced as an embodiment, in which magnetism is used for the adjustable positioning of the body part. Here, the repulsion of two or more permanent magnets between the body parts to be positioned, in case of the tongue between the posterior wall of the pharynx and the tongue body, or the attraction of two or more permanent magnets between the opposing body parts, in case of the tongue the tip of the lower jaw and the base of the tongue, exists. Preferably, in this connection, the elastic element exists in the form of magnetic discs or cuboids. The abutment is a compact magnet in the area of the spinal cord. The magnetic discs or cuboids can be inserted with opposite polarity directly underneath the mucosa at corresponding sites of the body parts to be positioned. The retraction of the magnetic bodies prohibits an approach of the body parts within the boundaries given by the magnetic force. In case of a positioning of a tongue body, the muscle force of the tongue exceeds the repulsive force of the magnet so that swallowing and speaking are not impaired. The magnetic bodies may be made of any magnetizable material. Preferably, they are embedded into a tissue-compatible material such as silicone and may be coated with active agents that promote the integration into the tissue and/or are bacteriostatic/bactericidal. Moreover, they may be doped so that they can be shown in imaging methods.

Examples for magnetic bodies are alloys of aluminum, nickel and cobalt (AlNiCo), ferrite magnets (i.e. sintered and subsequently magnetized mixture of barium or strontium oxide with ferrous oxide), alloys of the rare earth metal samarium and of cobalt (SmCo) or alloys by using neodymium, for example the alloy NdFeB (consisting of neodymium, iron and boron), which for improving the features may be ground to powder, pressed, sintered and provided with a surface coating in order to prevent corrosion. It is favorable, if the coercive field strength (which for the demagnetization capability or the tendency of a permanent magnet to lose the magnetic force by external magnetic fields) is relatively high. Thus, for example, a ferrite magnet has a three- to five-fold higher coercive field strength than an alloy of aluminum, nickel and cobalt, and alloys by using samarium have an about 14-times as high a coercive field strength as an alloy of aluminum, nickel and cobalt. Magnets by using neodymium have an about 17-times as high a field strength as alloys of aluminum, nickel and cobalt.

Preferably, modern permanent magnets are used. As opposed to ferromagnets, these are roughly indefinitely stable in case that they are kept within suitable temperature limits. In case of the human body temperature, this is granted in any case. The repulsive force and attractive force can be utilized. When using the repulsive forces by the completely implanted system according to the invention, two permanent magnets are implanted such that the magnetic force confers itself on the body tissues, the approximation of which would lead to disease symptoms. Implantation into the base of the tongue and into the posterior wall of the pharynx leads to a repulsion with movement of the tongue body forward. Conversely, the closer the tongue gets to the posterior wall of the pharynx, the more increases the repulsive force. Favorably, the magnets are chosen such that the repulsive force is negligibly small in resting position of the tongue and is not detectable by the patient.

Moreover, the magnets must be in a biocompatible form in order to effectively face the problems known in the art upon incorporation of materials that are foreign to the body. In addition, the magnets must be embedded gas-tight and liquid-tight and may be embedded or coated with bioinert or bioactive materials. Exemplary materials are silicones of different Shore hardness having a suitability for permanent implantation, polyethylene, polyurethane, polyester, PTFE, ceramics. Preferably, the materials must be soft and elastic in order to prevent an extrusion. Furthermore, the material shall have the material features postulated above, while having as small a material thickness as possible. Preferably, the magnet having a thickness of 2 mm and a diameter of 6 mm is discoidally shrink-wrapped in silicone Nusil 4845. The material thickness above the magnet is 0.5 mm, the maximal material thickness 2 mm, decreasing towards the ends to 0.2 mm. The length of the implant is preferably 15 mm and has a width of 7 mm. The magnet carrier (silicone) can take any shape. It may be circular, oval, elliptical, cross-shaped, star-shaped, rectangular, square or irregularly formed. Preferably, its geometry causes an optimal anchoring within the tissue. Other than disc-shaped magnets, magnets of any shape may be used. Typically, permanent magnets are cuboid, ball-shaped or rod-shaped. Suitable magnet sizes next to discs are in particular flat cuboids, e.g. in a size of 20×20×3 mm or 5×5×1.5 mm.

Instead of one magnet, also multiple magnets may be inserted into a carrier material. In this carrier material they may be arranged such that they correspond to the second carrier material at corresponding sites. One, two or also an array of magnets can be taken up from the carrier. In doing so, the repulsive force must be sufficiently high, which requires a minimum size of the magnet. Moreover, the device to be implanted must not exceed an agreeable maximal size.

More than two carriers with magnets may be implanted. Instead of two big ones several small carriers may be implanted as well. By suitable selection of the size (volume) and the remanence of the magnet, the different interests of the patients can be accounted for. For example a neodymium-iron-boron-(NdFeB) permanent magnet over a dimensioning of 20×20×3 mm develops a permanent repulsive force of 1 N at the distance of 16 mm. Upon implantation of the device according to the invention, in the pharyngeal space, further magnetic systems in the carrier system may be implanted into the sidewalls of the pharynx and into the edge of the tongue. In the completely implantable system, a carrier under a soft tissue cover of the posterior wall of the pharynx serves as reference point for the magnetic action. This reference point can also lie outside the body. This is the case in a partially implanted system. In this case, the patient carries a magnet implanted in the tongue tissue. The repulsive force of a further magnet (permanent magnet or electromagnet), which is positioned outside the body dorsal of the tongue, acting thereon, keeps the tongue in a distance which prevents the occurrence of apneas.

One magnet or an arbitrary amount of magnets may be employed. The crucial criterion is that the sum of the forces acting on the implanted magnet suffices to effectively prevent symptoms such as apneas, hypopneas and snoring produced by the approach of the body parts, for example the tongue and the posterior wall of the pharynx. It is essential that as homogenous a magnetic field as possible is generated in the respective target area by the form volume and amount of the magnets.

Since in case of a tongue implant the magnetic force must exclusively act during sleep, this embodiment would have the advantage that in the wakeful state the tongue can move free from any foreign influences. The magnet outside the body could be integrated into a neckband/headband or could be localized in the pillow of the patient. The fixation at the head of the patient has the advantage that the force always acts in the same direction and amount.

The electromagnetic field may also be regulated triggered by apnea. For example, in case of a decreasing early inspiratory flow averaged over several cycles of breathing, the field is adjusted up until the depth of breathing has again reached an individual defined value. The characteristics of regulation can be linear or progressive. The recording of the desired and actual values may be performed via thermal or acoustic sensors or via a pneumotachograph supported by a computer-aided real time signal processing and transfer of the control signals to an amplifier.

For example, a silicone carrier having two disc-shaped magnets (8 mm diameter, 3 mm thickness) is implanted into the base of the tongue of a patient. At night, an elastic and cushioned band which is suitable for taking up three permanent magnets of a dimensioning 20×20×13 mm is applied. The form of the band solely permits the desired position at the head of the patient. A strangulation is certainly ruled out. The repulsive force on the base of the tongue amounts to about 1 N at a neck circumference of 42 cm.

Instead of a band for taking up the external magnet, also a pre-shaped pillow may be equipped with the magnets such that their force acts in as short a distance as possible on the implanted (=internal) magnets. Pillows and neck rolls which fix the head within boundaries are commercially available, e.g.: Pilo®, neck support pillow Cervical from Dormabell, Kubivent Neck. Instead of a band, also a clip which is opened towards the front may be used which carries the magnets in slideable positions on a bar. The clip may correspond to head phones as regards form and holding function. The padded overlays are adjustable. They may seat on both sides of the zygomatic arch. The mounting bracket carrying the magnet lies against the skin of the nape, head and neck.

By suitably choosing the size (volume) and remanence of the magnet, it may be accounted for different needs of patients without the necessity of an intervention. The ideal feature of the magnet could be determined in a sleep laboratory with a freely adjustable electromagnet. The permanent magnet would be selected corresponding to the thus obtained results and be prescribed to the patient. In the head part of the bed of the patient/dorsal of the tongue in case of a desired repulsion, anterior of the tongue in case of a desired attraction, an electromagnet is localized which produces an electromagnetic field that is even over time and place.

At the same site, an electromagnet is localized which produces an electromagnetic field that is controlled over time and place.

The control/regulation is triggered by the normal mechanics of breathing.

The electromagnetic field is only switched on upon inspiration.

The control/regulation may also be triggered by the pathological mechanic of breathing. The electromagnetic field is only switched on upon apnea/hypopnea/snoring.

The magnets may further be incorporated into the collar of an especially manufactured pajama top. As opposed to common commercial pajama tops, the collar is characterized in that it is stiff enough not to kink. It is compatible to the skin and soft on the inside in order not to cause incompatibility reactions upon a demanded close contact. It has a connection towards shoulder-, back- and chest-section, which is stiff enough to enable a calculable position of the magnet-bearing collar portion. It has a connection to the shoulder-, back- and chest-section which is high enough to guarantee for a positioning of the magnet-bearing collar portion, if possible on the level of the base of the tongue. The collar can be taken off by means of customary methods (for example hook-and-pile fastener, zip fastener, buttons, built-in pocket). The pajama top is washable.

In case that the attractive force between the two magnet elements shall be utilized, the magnet-bearing fix point lies at a bone structure of the middle face or lower jaw. The attractive force of a magnet that is for example fixed at the lower jaw acts on a magnet which is implanted in the tissue of the tongue and/or in the tissue of the sidewalls of the pharynx or indirectly on the magnet carrier. Here, it is also possible to design the magnet carrier such that the force is transferred from a magnet that is not close to the surface of the tongue onto an implant, which mediates the force at the base of the tongue. This would have the advantage that the magnets would be more adjacent and, thus, the forces acting between them would be greater. A disadvantage of this embodiment is that the forces become smaller with increasing narrowness of the respiratory tube. For the treatment of snoring, the magnets may also be implanted at the soft palate.

The magnets shall be small, so that they cannot be perceived or can as little as possible be perceived as foreign bodies. They shall be exactly defined in their polarity and shall invariably be fixed within the tissue. Furthermore, they shall influence a sufficient volume of tissue in order to effectively keep the tissue at distance. They shall be positioned sufficiently tight underneath the approaching surfaces in order to be able to develop the biggest force as possible on each other. Moreover, they shall not show undesired side effects and may, where applicable, be contraindicated for carriers of implanted telemetric apparatuses such as pacemakers, shunt valves. Patients, who foreseeably require a magnetic resonance imaging need to be informed correspondingly and excluded from implantation.

With the implantable device by using the magnetic force, arbitrary body parts can be positioned. For example in lid paresis, the attraction of two magnetic systems which are implanted into the lid edges or close to the lid edges may be utilized. For this application, the lower lid is the abutment. Instead of suture fixation of the upper lid and the eyebrow upon palsy of the M. levator palpebrae, a magnetic system is also employable. Here, the abutment is located at the frontal bone.

In case of ptosis of the corner of the mouth caused by facial nerve paresis, a magnet at the upper jaw bone serves as fixing point/abutment, the second/the other ones, integrated in a carrier system, and either directly at the corner of the mouth or in connection with the corner of the mouth via a sling, move relatively to the fixing point.

In the area of the nasal valve, repulsive forces of two or more magnets are utilized. These are implanted in the region of the limen nasi such that the repulsion leads to a sufficient widening.

In any case, the carrier system must be shaped such that the magnets cannot perform a movement around their own axis even during a long time course. This is in particular of crucial importance in all instances, when repulsion is utilized.

Of particular importance is the positioning of body tissue in patients with incontinence problems. As well as in stool and urinary incontinence, particularly by employing the magnetic force, a locking mechanism can be achieved by the device according to the invention, which mechanism can be overcome by a certain opening pressure.

All parts of the device according to the invention can be produced in a basically familiar manner in a standard method for precision injection molding parts. Corresponding methods are well-known to a person skilled in the art. Depending on the form of the model, one or several cavities are milled. These are then filled with a silicone compound ("cavity injection molding form"-method).

Furthermore, the device of the invention may also be produced according to the spark discharge method. This method, which is known to a person skilled in the art, as opposed to stretching methods, has the advantage that significantly higher surface qualities are produced. The generation of a particularly smooth surface is of great importance for implantable parts. The smoother the surface, the smaller is the area which is exposed to inflammation reactions and enzymatic attacks. In the same way, the resistance of the relative movement declines therewith, and with it the wear. This reduces the risk of a bacterial colonization.

The following figures illustrate the device of the invention in more detail.

The device of the invention is used for the positioning of a human or animal body part in that the device is implanted into the corresponding body parts.

The device of the invention is particularly suitable for positioning a tongue body. Furthermore, also upper lid and lower lid may be positioned with the system upon loss of function/malfunction of the facial nerves. Likewise, the corners of the mouth can be brought into position upon facial nerve palsy. Moreover, a female breast can be lifted upon ptosis of the mamma, or nasal valves can be widened.

The device according to the invention is particularly advantageous for positioning the tongue within physiological boundaries. This is given by the fact that the anchor, at the base of the tongue, exerts a force into sagittal direction towards the tip of the chin via an elastic band and an abutment at the lower jaw. The device of the invention guarantees for a reliable, simple operative treatment of the sleep apnea syndrome. By the calculable system features, non-uniform successes of operation are avoided.

The operation method described in the following relates to the implantation of the device into a human tongue body/mouth floor. At this, the patient is positioned with reclined head. After disinfection of the skin at the neck, the mucosa of the mouth, and of the teeth, a preferably epinephrine-containing local anesthetic is given submentally and in the planned stitch channel towards the base of the tongue. Then, an about 3 cm long, frontal skin incision is performed 1 to 2 cm away from the tip of the chin. It is dissected to the lower jaw bone and the periosteum is detached. Furthermore, the abutment is fixed at the lower jaw in such a way that, later on, it is not perceived as disturbing by the patient.

With the target bow, the cut-out side at the base of the tongue is set. The trocar is cut out by means of the target bow in the tongue body and at the base of the tongue at the level of the linea terminalis (papillae vallatae). Starting from this side, the mucosa of the base of the tongue is undermined in order to give the implant space. For this, bent scissors or an angular knife developed for this purpose are used. Coming from the outside, preferably, a plaited or sturdy thread or wire with the dimensions 2×0 or 0 is threaded through the trocar, caught at the base of the tongue, and fixed at the implant (knot, plug connection). From the outside, the strand is put under traction, and at the same time the trocar is removed. In this way, the anchor strand is led outwards. The wings of the anchor are introduced into the mucosa tunnel, the mucosa is preferably closed with 3×0 or 4×0 vicryl-interrupted sutures. The implant is stretched strongly in order to check its rigidity and to guarantee the straight course of the strand. Now, the implant is hooked at the screw thus that a traction forwards arises which lifts off the tongue of the patient, who is relaxed and in dorsal position, from the posterior wall of the pharynx, or that at least a force of 1 N which is directed forwards can be read off the force measuring device. This device is hooked into one of the free recesses of the implant. The implant is shortened by an amount that still enables a decrease of the tension by the set degree. Preferably, a two-layered wound closure with 4×0 vicryl subcutaneous interrupted sutures, 4×0 or 5×0 cutaneous suture, is carried out. In male patients, this is preferably made in form of a continuous intracutaneous suture, in order not to produce any obstacle during shaving. The wound is bandaged. Intraoperatively and postoperatively, yet at least perioperatively, the patient obtains an antibiotic (for example cephalosporin). A postoperative observation is carried out, at least with oxygen monitoring, as well as a laboratory chemical control of the inflammation parameters.

According to a further embodiment of the operation technique, the elastic element is inserted in Seldinger technique. In doing so, a trocar is pushed forward from submentally up in the submucosal space. A wire is pushed forward through the trocar and, by means of the form of the interior of the trocar, is deflected towards the side upon leaving the trocar. The wire intrudes through the musculature all the way to the edge of the tongue. The trocar is removed. Over the wire, an elastic module is pushed forward until the target region is reached. The wire is removed. Via the newly inserted trocar, that has been turned by 90° and/or 180° in its longitudinal direction, the procedure described above is repeated until sufficient elastic elements are placed in the tongue in order to be able to mediate the necessary traction to sufficient tissue of the tongue in direction to the tip of the chin. The bodies that are introduced into the tongue via this route can later be influenced, for example, by correction of a pretension, introducing of a core or by thermal or chemical methods.

Instead of a trocar with only one guidance, also a trocar incorporating all guidances required may be used. A respective greater outer diameter would need to be accepted, in exchange, the trauma for repeated insertion ceases to exist.

According to a further embodiment of the operation technique, an own canal is intended for each elastic element to be inserted. The trocar can remain in situ. Ideally, the tip consists of a resorbable material. Also the walls of the trocar may consist of resorbable material.

As far as a magnet carrier system is to be implanted, the magnet carriers are preferably implanted submucosally, subfacially or intramuscularly. In order to maintain the minimally invasive character of the method, the following method has proven itself: a 1.5 cm long craniocaudal mucosa incision is performed laterally in the pharynx, undermined up to the desired length with an angular knife provided therefor. A sturdy thread is led through the tissue tunnel. The attached carrier is pulled through thus far until it completely lies in the wound. The strand is cut, the mucosa wound is closed. The procedure at the base of the tongue is analogous to that.

With the described implantation of the device according to the invention, in particular, obstructive sleep-related breathing disorders can effectively be treated. Further indications for an implantation of the device according to the invention are the upper airway resistance syndrome, obstructive snoring, heavy snorer syndrome, glossoptosis, macroglossia in trisomy 21, pathological enlargements of the tongue, for example acromegaly as consequence of a hypophysial disorder.

The following examples further illustrate the subject-matter of the invention.

THERAPEUTIC EXAMPLES

The patients who in the following were treated with the device of the invention had either gone through an nCPAP-attempt without success, or opposed to the nCPAP-treatment. In all cases, a sleeping apnea syndrome was polysomnographically confirmed. No anatomic anomalies, severe malocclusion situations or space-demanding processes of the upper airways were existent. The patients were informed in writing about the healing attempt during two informational conversations. The written consent of the patients was obtained.

Example 1

For many years, the patient suffered from excessive daytime tiredness, showed a tendency to fall asleep when driving and during work, and complained about a restriction of life quality. Several conservative therapeutic attempts (nCPAP) proved in vain.

The device according to the invention was implanted according to the description above. The first implant consisted of a silicone trachealstent (Dumon) and a silicone lacrimal duct intubation ("Silikonträndenwegsschienung") (Guibor lacrimal duct gap maintainer). The attachment at the lower jaw was carried out via a Mitek-anchor and the knot connection was made with the silicone double threads. The healing procedure turned out uncomplicated.

On his own request, the patient left the hospital prematurely and immediately thereafter started to work again. He felt considerably more efficient and more awake, during daytime he no longer showed a tendency to sleep, and he reported about an improved quality of life.

Example 2

The patient had a history of many years of a sleeping apnea syndrome with morning tiredness, daytime tiredness, tendency to fall asleep and low efficiency. He had gone through several unsuccessful attempts of nCPAP and rhinosurgery.

The device according to the invention was implanted according to the description above. As opposed to the previous example, the elastic element consisted of a silicone band from retinal surgery. The connection between anchoring plate (out of a prepared tracheal stent) and the silicone band was carried out via a Gore-Tex thread. At the lower jaw, the connection was made by means of a titanium screw and a non-resorbable thread that was stitched through the band and knotted at the screw.

After a short time, the patient reported about a subjective improvement of the daytime tiredness.

Example 3

The patient had a multi-year history that was characterized by severe daytime tiredness, tendency to fall asleep during driving and during work and weak efficiency. In addition to conservative therapy with nCPAP, a surgery of the soft palate had been performed, however without success. The same operation method as in Example 2 was performed. The silicone band was clamped to the lower jaw via a titanium plate. Postoperatively, no complications were observed. At the third day after the surgery, the patient was released and, shortly thereafter, reported about the subjective improvement of daytime tiredness. Since no complete restitutio was achieved, a further stretching of the thread was necessary.

None of the patients showed an undesired effect of the method. The postoperative pain turned out significantly lower than in case of the repose method of the prior art. The anatomically practicably configured anchoring plate and the easily adjustable tension of the thread, that further improved the results, turned out advantageous. The success of treatment yielded by an implantation of the system according to the invention, in the treatment results, proved superior to the operational procedures of the prior art (repose, hyoid suspension, UPPP, somnoplasty).

The invention claimed is:

1. A device for central implantation into a tongue body, comprising:
    an elastic element comprising an anchor and an elastic band configured to exert a tensile force that lifts the tongue body off a posterior wall of the pharynx,
    wherein the elastic band includes a plurality of holes extending and aligned along the center of a length of the elastic band allowing for fixing the elastic band at different positions at an abutment to increase or decrease said tensile force, such that the tensile force can be adjusted in order to allow for a desired, predetermined setting of the device while implanted, and
    wherein the device is composed of non-resorbable material.

2. The device of claim 1, wherein the elastic band is implemented as a polyhedron, a sphere, or part of a sphere.

3. The device of claim 2, wherein the elastic band has a pair of edges which are rounded.

4. The device of claim 1, wherein the plurality of holes are round, oval, or polygonal openings that reach through a section of the elastic band.

5. The device of claim 4, wherein a thin material lamella is provided in a middle of a cross-section of the plurality of holes.

6. The device of claim 1 wherein the anchor has a round, elliptic or oval form.

7. The device of claim 1 wherein the anchor has perforations.

8. The device of claim 1 wherein the anchor is doped with a contrast-giving material.

9. The device of claim 1 wherein the anchor has a material thickness and a peripheral region, wherein the material thickness decreases towards the peripheral region.

10. The device of claim 1 wherein the anchor is straight.

11. The device of claim 1 wherein the anchor is bent.

12. The device of claim 1 wherein the abutment is a screw, a clamping, an electromechanical locking or a combination of base and locking cap.

13. The device of claim 1, wherein the elastic band of the elastic element is a band having a fish scale structure.

14. The device of claim 1, wherein the elastic band is removably attached to the anchor.

15. The device of claim 1, wherein the device is made of plastic.

16. The device of claim 1, wherein the device is made of silicone.

17. A method for treatment of a disorder caused by a deficient or inadequate positioning of a human or animal tongue body, comprising:
    implanting into the tongue body of the human or animal, a device comprising:
    an elastic element comprising an anchor and an elastic band configured to exert a tensile force that lifts the tongue body off a posterior wall of the pharynx,
    wherein the elastic band includes a plurality of holes extending and aligned along the center of a length of the elastic band allowing for fixing the elastic band at different positions at an abutment to increase or decrease said tensile force, such that the tensile force can be adjusted in order to allow for a desired, predetermined setting of the device while implanted, and
    wherein the device is composed of non-resorbable material.

18. The method of claim 17 wherein the device is implanted within a patient.

19. A method for treatment of a breathing disorder, sleep-related breathing disorder, obstructive snoring and/or glossoptosis in a subject, comprising:
    implanting into a tongue body of the subject a device comprising:
    an elastic element comprising an anchor and an elastic band configured to exert a tensile force that lifts the tongue body off a posterior wall of the pharynx,
    wherein the elastic band includes a plurality of holes extending and aligned along the center of a length of the elastic band allowing for fixing the elastic band at different positions at an abutment to increase or decrease said tensile force, such that the tensile force can be adjusted in order to allow for a desired, predetermined setting of the device while implanted, and
    wherein the device is composed of non-resorbable material, and wherein the device is removable.

20. The method of claim 19 wherein the device is implanted within a patient.

* * * * *